United States Patent [19]

Sarkar et al.

[11] Patent Number: 5,683,866

[45] Date of Patent: Nov. 4, 1997

[54] PROCESS FOR PRODUCING A TARGETED GENE

[76] Inventors: Debi P. Sarkar, C-1/121, Janakpuri; Komal Ramani, C-1-A/67A, Janak Puri, both of P.O. Janakpuri, New Delhi-110058; Roop Singh Bora, 215-E, Pocket-I, Mayur Uihar Phase-I, Delhi-91; Mukejn Kumar, 230/26E, Kalyan Marg, Mandanali- fazalpur, New Delhi 110092; Sandeep K. Tyagi, A-233 New Ashok Nayar, New Delhi-110096, all of India

[21] Appl. No.: 647,312

[22] Filed: May 9, 1996

[51] Int. Cl.$^6$ .............................. C12Q 1/70; C12N 7/06; C12N 7/02; C12N 5/08

[52] U.S. Cl. .................. 435/5; 435/238; 435/239; 435/370

[58] Field of Search .................. 424/93.21, 450; 435/69, 91.1, 172.1, 235.1, 240.1, 5, 238, 239, 370; 436/829; 514/2, 44; 536/23.1

[56] References Cited

PUBLICATIONS

Bagai and Sarkar. Fusion–mediated microinjection of lysozyme into HepG2 cells through hemmaglutinin neuramidase–depleted sendai virus envelopes. J. Biol. Chem.. vol. 269(3):1966–1972. Dec. 21, 1994.

Tomita et. al.. Direct in–vivo gene introduction into rat kidney. BBRC. vol. 186(1):129–134. Jul. 15 1992.

*Primary Examiner*—David Guzo
*Assistant Examiner*—William Sandals
*Attorney, Agent, or Firm*—Spencer & Frank

[57] ABSTRACT

This invention relates to a reconstituted sendai-viral envelope containing the F-protein (F-virosomes) and to a process for producing a targeted gene or drug delivery carrier produced by the steps of chemical reduction of Sendai virus for reduction of HN protein and subjecting the reduced virus to the step of dialysis for removal of the reducing agent. The reduced virus is then solubilized with a detergent to obtain a solution. The said solution is centrifuged to separate the insolubles consisting of reduced HN protein and core of the virus, adding the required specific gene or drug to the centrifugal solution. Finally, the detergent is removed using an affinity complex agent which binds the detergent leading to the formation of the delivery carrier.

22 Claims, 7 Drawing Sheets

PROCESS FOR PRODUCING A TARGETED GENE

FIELD OF THE INVENTION

This invention relates to a process for producing a targeted gene or drug delivery carrier.

By way of example, the carrier used for delivery of chloromphenicol acetyl transferase gene (CAT gene) to HepG2 cells and the expression of the CAT gene in the human hepatoblastoma cells (HepG2).

PRIOR ART

A major problem in the delivery of DNA and other biological macromolecules into cells is the crossing of the permeability barrier imposed by the plasma membrane. In the prior art, numerous carriers have been employed in the search for an effective delivery system that may allow the transfer of their contents into the cytoplasm of specific cells. In the past few years closed lipid bilayer vesicles (lipsomes) had been used for delivering various macromolecules into the living cells. They protect encapsulated molecules from degradation and can be used to entrap bioactive molecules of diverse nature. In this system, the target molecules and liposomes are taken up by endocytosis and are released in lysosomes. In many cases, the intralysosomal low pH environment and the lysosomal enzymes cause hydrolysis and inactivation of the enclosed material. Another delivery system is based on retroviral vectors. Although this system has a higher transformation efficiency than liposomes, the viral oncogenes and the random insertion of the retroviral genes into the host genome have undesirable side effects besides inherent cytopathicity. Moreover retroviral vectors lack cell type specificity, since non-specific targeting to normal cells is a major obstacle for cytotoxic drugs and genes in cancer and gene therapy respectively.

Various delivery systems have been suggested in the art for carrying a gene to the cell in the instance of a malfunctioning of a gene or a malfunctioning of a particular cluster of genes. One such delivery system consists of a adenovirus carrier for the gene. The gene enters the nucleus through the endosome, and then expresses itself using the machinery of the cell and produces the specific protein. A disadvantage associated with such a known delivery system is that it is not specific to cells of target. Yet another disadvantage is that the virus exhibits cytopathogenicity. A further disadvantage is that the gene is degraded while passing through the endosome and thereby reducing efficiency.

Yet another delivery system suggested in the art comprises artificial membrane bound vesicles having the characterised gene, which also enters the endosome and DNA is released to the nucleus. A disadvantage of such a delivery system is that the gene gets substantially degraded upon entering the endosome. Thus, due to the aforesaid disadvantages, such delivery systems have not been suitable for therapy.

It is known that reconstituted Sendai viral envelopes (F,HN-virosomes) can be used for selective delivery of biologically active molecules and drugs into the cytoplasm, bypassing the lyososomal route. F,HN-virosomes containing two glycoproteins, F (fusion protein) and HN (Hemagglutinin-neuraminidase) are known to fuse efficiently with the plasma membrane of target cells and have served as excellent carrier vehicles for fusion mediated microinjection of macromolecules such as DNA, RNA, toxins and polypeptides into cultured cells. Such delivery utilises the binding property of HN to the sialic acid residues of the membrane, followed by the F protein mediated fusion of the viral envelopes with the host cell plasma membrane at neutral pH. In one of the invivo studies, liposomes-red blood cell ghosts-Sendai virus complex had been successfully used to introduce and express foreign DNA into the nuclei of adult rat liver cells. Using this delivery system, human insulin gene was reported to be expressed in intact rat liver. However, such a virus complex was attended with the disadvantage that it did not possess any target or specificity characteristics and whereby the virus did not possess any advantageous carrier or delivery properties. Further, the known virus complex contained constituents which may result in undesired side effects.

OBJECTS OF THE INVENTION

An object of this invention is to propose a process of producing such a gene or drug delivery carrier from Sendai virus.

Another object of this invention is to propose a process of producing such a gene or drug delivery carrier from Sendai virus which is efficient.

Another object of this invention is to propose a delivery system which obviates the disadvantages associated with those of the prior art.

Yet another object of this invention is to propose a delivery system which is non-pathogenic to humans.

Still another object of this invention is to propose a delivery system which allows genes to be delivered intact and are able to express biologically active protein products.

DESCRIPTION OF THE INVENTION

According to this invention, there is provided a process for producing a targeted gene or drug delivery carrier comprising the steps of:

i. chemical reduction of Sendai virus for reduction of HN protein;

ii. subjecting the reduced virus to the step of dialysis for removal of the reducing agent;

iii. solubilizing the reduced virus with a detergent to obtain a solution;

iv. centrifuging the solution to separate the insolubles consisting of reduced HN protein and core of said virus;

v. adding the required specific gene or drug to the centrifuged solution;

vi. slowly removing the detergent with an affinity complex agent which binds the detergent leading to the formation of said delivery carrier.

In a further embodiment of this invention is provided a process for the delivery of DNA and other biological macromolecules into HepG2 cells using F-virosomes comprising in the steps of:

i. growing Sendai virus (Z-strain);

ii. harvesting and purifying the Sendai virus by any known method;

iii. preparing reconstituted Sendai viral envelopes containing the F-protein (F-virosomes);

iv. loading the reconstituted Sendai virus with DNA and other biological macromolecules to obtain loaded F-virosomes;

v. incubating loaded F-virosomes with HepG2 cells for membrane-fusion activity to deliver the DNA and other biological macromolecules to the HepG3 cells.

In accordance with this invention, a Sendai virus is employed as the carrier. A Sendai virus is known in the art which is an enveloped animal virus. Such a virus is not pathogenic to human body, and has a membrane with two classes of protein, namely a fusion protein (F) and a hemagglutinin-neuraminidase (HN) protein. It has now been found that if both the aforesaid proteins are present, then the carrier or virus does not have a specific target property. In effect, such a virus has target insensitive properties.

In accordance with the present invention, if the HN protein is removed and the virus is retained with the shell or membrane along with F-protein and the desired gene or drug then incorporated or implanted therein, the desired properties are achieved. In fact, it has now been found that a removal of the HN protein provides the desired target properties.

The present invention provides a rational and quantitative approach of targeted delivery and expression of a foreign reporter gene into liver cells.

In culture using the modified Sendai viral envelopes (F virosomes) with the added advantage of avoiding degradation of the entrapped DNA caused by the endocytotic pathway. The target specificity of F-virosomes has been ensured by the strong interaction between teriman B-galactose moiety of F protein and ASGP-R on membrane of HepG2 cells. It has also been found that F protein of F-virosomes behaves both as a ligand and a membrane fusogen for targeting of virosomal aqueous contents (e.g. hygromycin B and lysozyme) to to the cytosolic compartment of liver cells. It has now been established that heat treatment of F protein in F-virosomes completely abrogates its fusogenic potential without significantly affecting the galactose-mediated specific recognition of ASGP-R. This has been an important control to use heat treated F-virosomes loaded with DNA, as liganded protcoliposomes, which may be efficiently endocytosed by HepG2 cells. This path has been compared with that of fusion-mediated delivery of DNA by F-virosomes. The amount of DNA delivered by fusion mode is more than that by liganded protcoliposomes (heat-treated F-virosomes) as detected by a stronger hybridization signal. Thus, the specificity and the increased efficiency of this DNA delivery vehicle is present. Further evidence of fusion-mediated delivery of pCIS3CAT DNA comes from the quantitation and expression of functional CAT protein inside HepG2 cells, the expression of CAT has been quantitated by an extremely sensitive and specific ELISA method and compared with that of other conventional delivery methods. The heat-treated F-virosomes are found to be partially active in terms of CAT expression. This conforms to the DNA delivery mode. It could be explained as escape of some DNA molecules from being degraded inside endocytotic vescicles of HepG2 cells in case of heat-treated F-virosomes. More striking is the comparison with lipofectin mediated translocation of HepG2 cells with pCIS3CAT DNA. In F-virsome mediated delivery, 1ug of encapsulated DNA is sufficient for detectable expression of CAT whereas 15 μg DNA is required in case of lipofectin mode, HepG2 cells preincubated with asiaiofetuin fail to express any detectable CAT protein 24 h, showing thereby the targeted nature of this F-virosomal delivery system. This system is further comprehended by the expression of enzymatically active CAT protein.

The delivery vehicle of this invention has immense potential for delivery genes of therapeutic importance to liver cells in vivo and such delivered genes retain their potential of expression into gene products by utilising the natural gene expression machinery of the target cells.

BRIEF DESCRIPTION OF THE DRAWINGS

This invention will now be explained in greater detail with reference to the accompanying drawings and the examples.

A: Subcellular fractions of HepG2 cells incubated with F-virosomes containing 1 μg of DNA.

B: Subcellular fractions of HepG2 cells incubated with F-virosomes containing 10 μg of DNA.

C: Subcellular fractions of HepG2 cells incubated with heat-treated F-virosomes containing 1 μg of DNA.

D: Subcellular fractions of HepG2 cells incubated with heat-treated F-virosomes containing 10 μg of DNA.

Figure 3A:
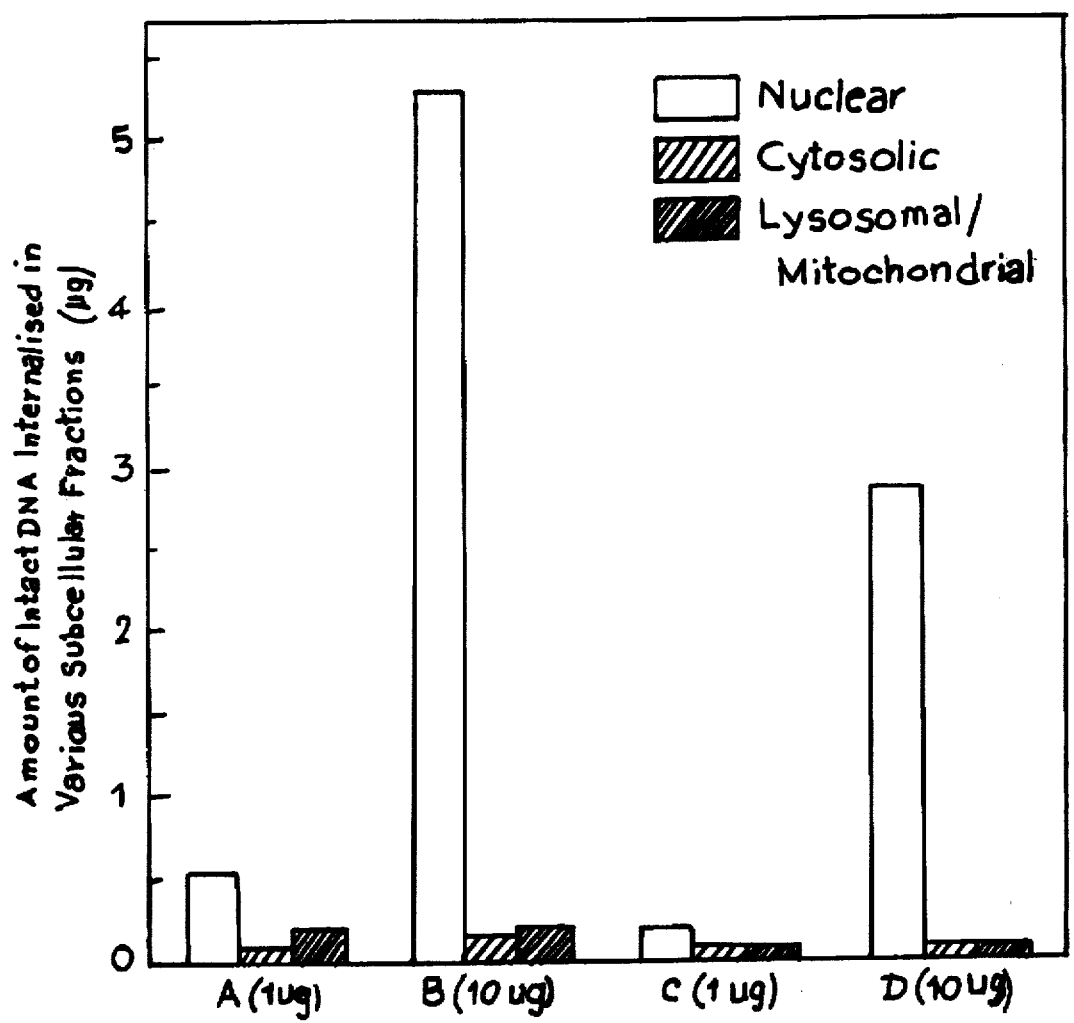
FIG. 3a refers to subcellular distribution pattern of $^{32}P$-labeled pCIS3CAT DNA delivered to HepG2 cells by F-virosome mediated microinjection. HepG2 cells were incubated with DNA loaded F-virosomes (0.3 mg of F protein, 1 μg of DNA, 3.0 mg of F protein, 10 μg of DNA), and the corresponding heat-treated DNA loaded F-virosomes (56° C., 30 min.) at 37° C. for 2 h. After 2 h of fusion, cells were further incubated for 24 h at 37° C./5% CO. Subcellular fractionation of HepG2 cells ($4\times10^7$) was carried out as described in the text. Fractions were assayed for radioactivity. Values are mean of duplicate determinations.
Figure 3B:
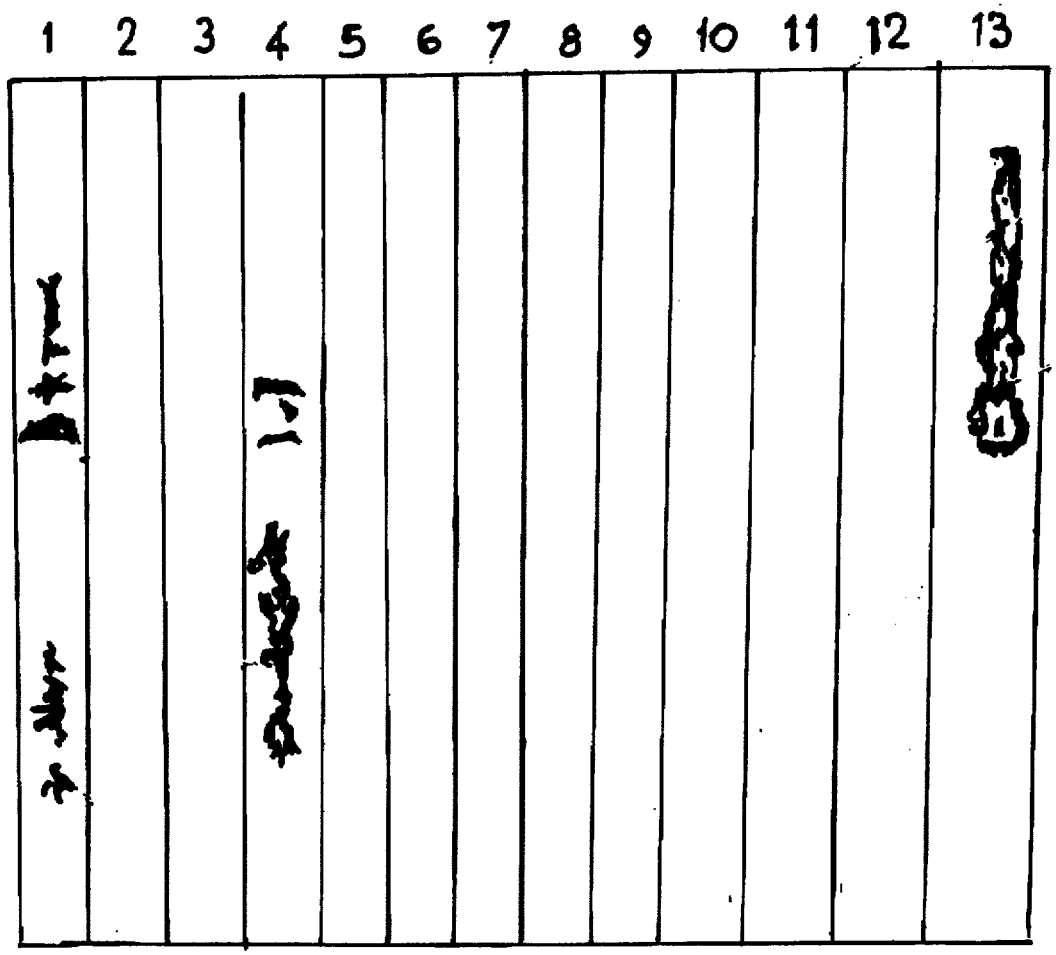

FIG. 3b refers to southern hybridization of pCIS3CAT DNA delivered to the various subcellular fractions using $^{32}P$-labeled CAT gene fragment as a probe. HepG2 cells were incubated with DNA loaded F-virosomes (0.5 mg of F protein, 1 μg of DNA) and heat-treated F-virosomes (56° C., 30 min) at 37° C. for 2 h. After 2 h of fusion, cells were further incubated for 24 h at 37° C./5% CO. Subcellular fractionation of HepG2 cells was carried out as mentioned in the text and DNA from various fractions was hybridized with P-labeled CATgene probe. Lanes 1,2,3 represent DNA from nuclear, cytosolic and lysosomal/mitochondrial fractions respectively of HepG2 cells incubated with DNA loaded F-virosomes. Lanes 4,5,6 represent DNA from nuclear, cytosolic and lysosomal/mitochondrial fractions respectively HepG2 cells incubated with DNA loaded heat-treated F-virosomes. Lanes 7,8,9 represent DNA from nuclear, cytosolic and lysosomal/mitochondrial fractions respectively of HepG2 cells treated with free DNA. Lanes 10,11,12 represent nuclear, cytosolic and lysosomal/mitochondrial fractions respectively of HepG2 cells alone. Lane 13 corresponds to pCIS3CAT DNA (700 ng).

Figure 4A:
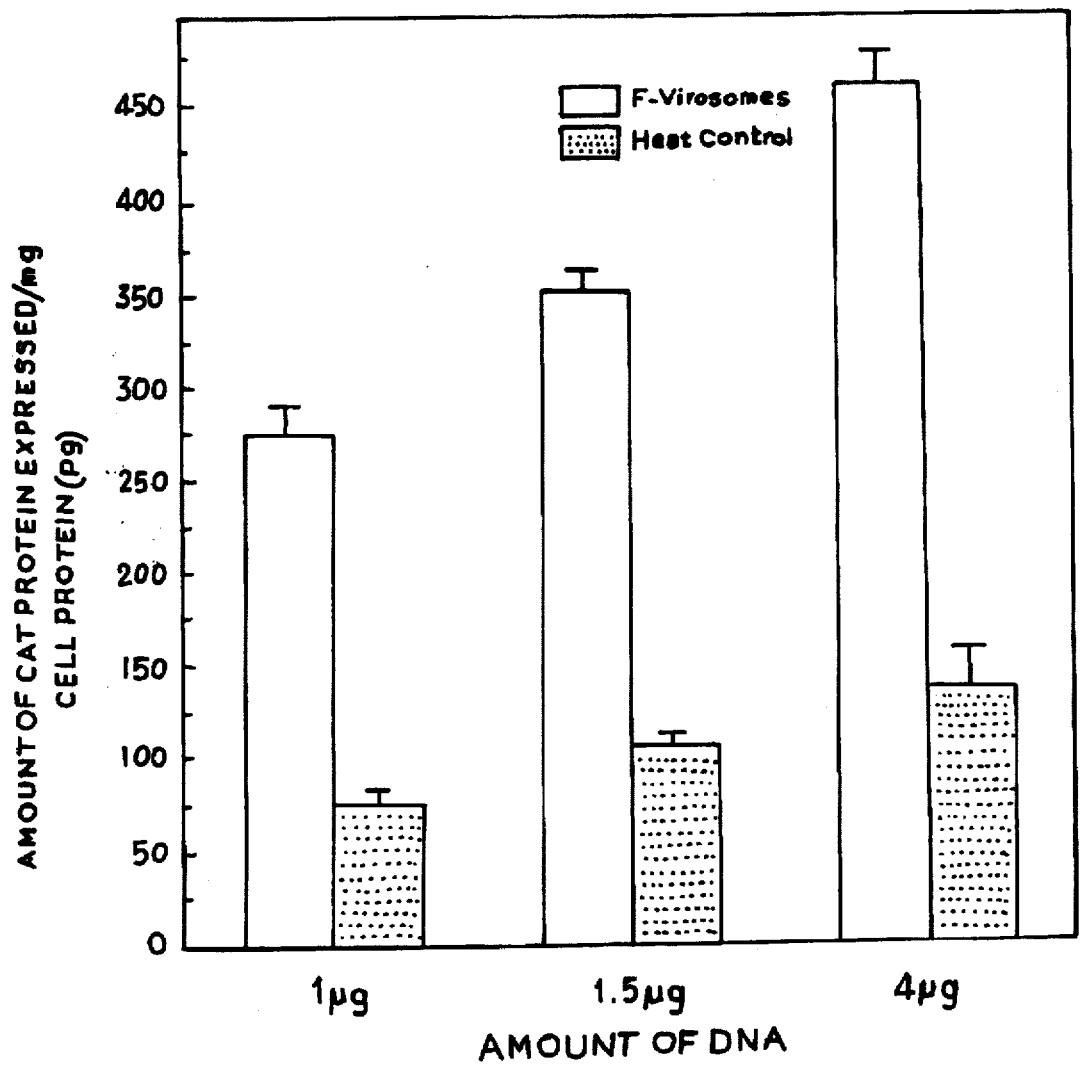

FIG. 4a refers to dose dependent expression of pCIS3CAT DNA delivered to HepG2 cells by F-virosomes: HepG2 cells were incubated with loaded F-virosomes (0.5, 0.7 and 1.8 mg of F protein) containing varying amounts of DNA (1, 1.5 and 4 μg and the corresponding heat controls. After 2 h of fusion, cells were further incubated for 24 h at 37° C./5% CO. After 24 h of growth, cell extracts were prepared and CAT ELISA was performed as described in the text. The amount of CAT protein expressed per mg of cell protein was determined.

Figure 4B:
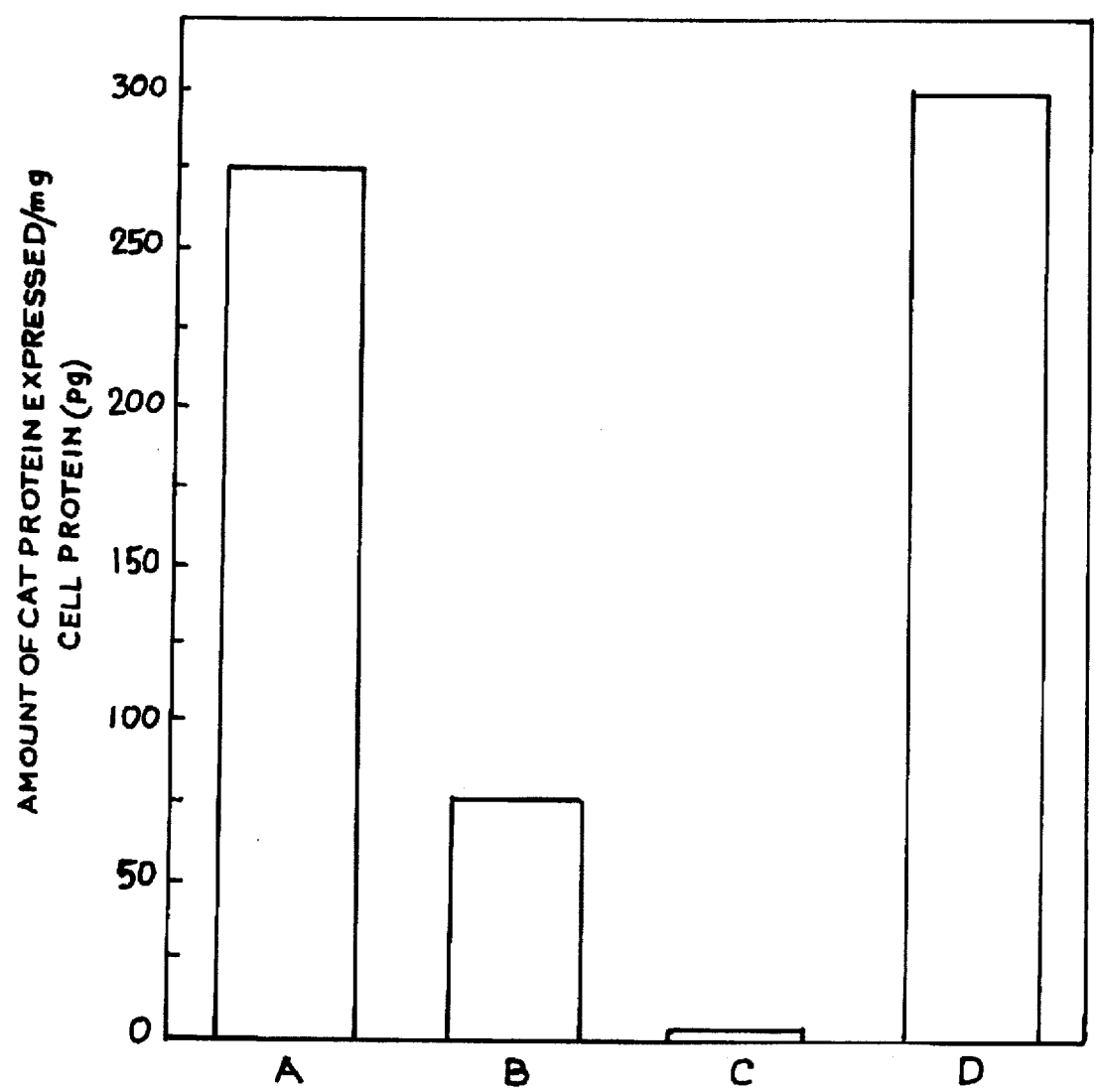

FIG. 4b. Comparison of F-virosome and lipofectin mediated DNA delivery systems: HepG2 cells were incubated with F-virosomes containing 1 μg of pCIS3CAT DNA and the corresponding heat control and CAT expression was compared to that of lipofectin mediated DNA delivery.

A represents amount of CAT protein expressed after delivery of 1 μg of DNA by F-virosomes.

B represents amount of CAT protein expressed after delivery of 1 μg of DNA by heat-treated F-virosomes.

C represents amount of CAT protein expressed after delivery of 1 μg of DNA by lipofectin mode.

D represents amount of CAT protein expressed after delivery of 15 μg of DNA by lipofectin mode.

Figure 5:
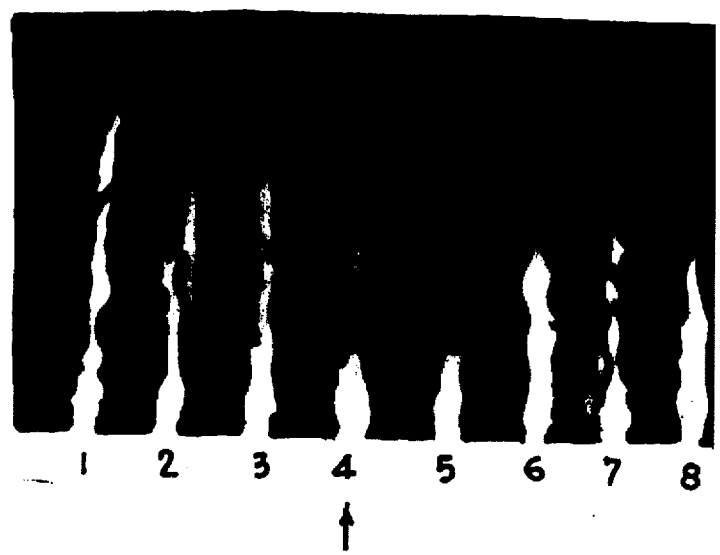

FIG. 5 refers to enzymatic activity of CAT protein expressed in HepG2 cells after delivery of pCIS3CAT DNA by fusion mode: Loaded F-virosomes (2 mg of F protein containing 7 μg of DNA) were incubated with HepG2 cells. The assay protocol has been described in the text. Lane 1, extract from F-virosome incubated cells (100 μg protein); Lane 2, extract from F-virosome incubated cells (350 μg protein); Lane 3, extract from F-virosome incubated cells (700 μg protein); Lane 4, extract from cells incubated with free DNA (700 μg protein); Lane 5, extract from cells alone (700 μg protein); Lane 6, reference standard containing all three acetylated derivatives of BODIPY-chloramphenicol; Lane 7, CAT standard (50 pg); Lane 8, CAT standard (500 pg). BCAM, BODIPY-chloramphenicol; AcBCAM, acetylated BODIPY-chloramphenicol.

DETAILED DESCRIPTION OF THE PREFERRED EMBODIMENTS

Preparation of F-virosomes loaded with pCIS3CAT DNA:

Reconstituted Sendai viral envelopes containing the F protein (F-virosomes) were prepared as described earlier. The TritonX-100 solubilised fraction of virus was mixed with pCIS3CAT DNA (75 μg of DNA per mg of viral protein) and reconstituted by stepwise removal of detergent by adding SM2 BIOBEADS® (a nonpolar polystyrene aadsorbent) in a ratio of 1:8 (Detergent:biobeads,w/w) for a period of 6 h. The unentrapped DNA absorbed on the outer surface of virosomal membrane was removed by treatment of virosomes with DNAaseI (60 μg/mg of protein) at 37° C. for 30 min. The presence of entrapped DNA was checked by lysing virosomes with 2% SDS, loading on 0.8% agarose gel and subsequent staining with ethidium bromide. The amount of DNA entrapped in F virosomes was calculated using $^{32}$P-labeled pCIS3CAT DNA. Membrane fusion activity of loaded F-virosomes was ascertained by their ability to bring about lysis of mouse RBCs in the presence of wheat germ agglutinin according to our published procedure. Stability of loaded F-virosomes was checked by leakage of DNA during incubation with PBS, with fresh mouse plasma and 10% FCS (in DMEM) at 37° C. for 16 h and at 56° C. for 30 min (heat-treatment). Purity of F-virosomes preparation was checked on 10% SDS-PAGE.

Fusion mediated delivery of pCIS3CAT DNA to HepG2 cells:

Quantitation of $^{32}$P-labeled pCIS3CAT DNA delivered in various subcellular fractions: HepG2 cells were grown in monolayers, in T-25 flasks till a density of 1×10 cells. Monolayer cells were washed thrice with 2 ml of DMEM without serum. Cells were incubated with loaded F-virosomes (0.3 mg of F protein, 1 μg of DNA and 3 mg of F protein, 10 ug of DNA in 4ml of DMEM without serum) for 2 h at 37° C./5% $CO_2$ Heat-treated F-virosome-cell mixtures were used as controls. After 2 h of fusion, medium was replaced with DMEM containing serum (10% FCS) and cells were further incubated for 24 h at 37° C./5% $CO_2$. Parallel flasks were made for cell counting after 24 h of growth. After 24 h, cells were washed four times with 2 ml of ice cold DPBS containing 5 m EDTA for stripping off the virosomes bound (not fused) to cells. Monolayer cells were lifted with 0.5 ml Trypsin-EDTA (0.05% Trypsin, 0.53 mM EDTA) and washed with 1.5 ml of ice cold TBS. Cell suspension was centrifuged at 3000 rpm for 10 min at 4° C. Cell pellet was resuspended in 1 ml of 0.01M Tris-HCl (pH 7.4) containing 0.25M sucrose Cells were dispersed in homogeniser of Potter-Elvehjem type at 4° C. with 15 up and down strokes. The separation of nuclear and lysosomal/mitochondrial fractions was carried out at 600 g and 1500 g at 4° C. for 10 min and 30 min respectively. After separation of lysosomal/mitochondrial fraction, cytosolic fraction was obtained. The nuclear and lysosomal/mitochondrial pellets were resuspended in 500 ul of TE buffer (10 mM Tris-HCl, 1 mM EDTA, pH 8.0) and passed through G26 needle 4 times. Aliquots of the fractions were spotted on glass microfiber filters (Whatman International Ltd., Maidstone, England) and the TCA (Trichloroacetic acid) precipitable counts were measured. The amount of DNA internalized in the various sub-cellular fractions was determined from the specific activity of the P-labeled DNA.

Evaluation of the integrity of the delivered DNA in various subcellular fractions by Southern hybridization: HepG2 cells (grown in monolayers) were incubated with DNA loaded F-virosomes (0.5 mg of F protein 1 μg of DNA in 4 ml of DMEM without serum) for 2 h at 37° C./5% $CO_2$. Subcellular fractionation of HepG2 cells was carried out as described above. DNA (50 μl) from each fraction was electrophoresed on 0.8% agarose gel and transferred to nylon membrane. The blot was hybridized with $^{32}$P-labelled 1.5-kb Xhol-Smal fragment harbouring the CAT gene. Hybridization was done according to a standard protocol. Membrane was exposed to X-Ray film at −70° C. for 4 days.

Expression of CAT gene in HepG2 cells: HepG2 cells were grown in mololayers till 50% confluence was attained. Loaded F-virosomes (0.5 mg, 0.7 mg and 1.8 mg of F protein containing 7 μg of pCIS3CAT DNA for CAT assay) were incubated with HepG2 cells in 2 ml of DMEM without FCS at 37° C./5% CO. After 2 h of fusion, medium was replaced by 4 ml of DMEM containing 10% FCS and cells were further grown for 24 h at 37° C./5%CO. Heat-treated F-virosome-cell mixtures, F-virosome-cell mixtures incubated with 2 mg/ml asialofetuin, free DNA-cell mixtures and cells alone were taken as controls for both CAT ELISA and CAT assay. Lipofectin mediated transfection of HepG2 cells with pCIS3CAT DNA was performed following standard protocol.

Preparation of cell extracts: Cell extracts were made 24 h after DNA delivery by sonicating the washed cells in 200 μl of 0.25M tris-HCl (pH 7.5), containing 2 mM PMSF and 10 μg/ml of aprotinin. After the cells were spun at 3000 rpm for 15 min. at 4° C., the protein amount in the supernatant was estimated by Bradford method. This supernatant was used to perform CAT ELISA and CAT assay.

CAT ELISA: CAT ELISA was carried out by a protocol (Sandwich immunoassay) as suggested by manufacturer (Boehringer Mannheim, GmBH, Germany). Amount of CAT protein expressed by fusion mediated delivery of DNA was determined. Determination of CAT activity (CAT assay): CAT assay was performed using fluorescent BODIPY™-chloramphenicol substrate provided in the Fluoreporter FAST CAT assay kit. Cell extracts were heated at 65° C. for 5 min prior to use. The assay mixture contained varying amounts of cell extracts, 10 μl of 1 mM BODIPY-Chloramphenicol and 20 μl of 4 mM acetyl-CoA in a final volume of 200 μl. Standard CAT enzyme (50 μg and 500 μg) was used as a positive control for CAT assay. Cell extracts prepared from cells incubated with free pCIS3CAT DNA and cells alone were used as controls. All the regents except acetyl-CoA were preincubated together for 5 min at 37° C. After equilibration was reached at this temperature, the reaction was started by adding acetyl-CoA and allowed to proceed for 10 h at 37° C. The reaction was stopped by adding 0.8 ml of cold ethyl acetate. The organic phase was separated from aqueous phase, dried and resuspended in 10 μl of ethyl acetate. The samples were spotted on silica gel thin layer plates and run with chloroform:methanol (90:10, ascending). 10 μl of reference standard containing all three acetylated products of BODIPY-caloramphenicol was also run as a marker along with the samples to identify the position of spots in experimental samples.

Figure 2:
FIG. 2 refers to agarose gel electrophoresis of pCIS3CAT DNA entrapped in F-virosomes. 20 μl, of F-virosome (20 μg protein having 0.1 μg DNA) sample was lysed with 2% SDS, loaded on 0.8% agarose gel and run at 100V for 1 h. The bands were visulised after staining the gel with ethidium bromide. Lane 1, Free pC1S3CAT DNA (1 μg); Lane 2, Entrapped pCIS3CAT DNA before DNAase treatment; lane 3, Entrapped pCIS3CAT DNA after DNAase treatment.

Characterization of DNA loaded F-virosomes: F-virosome preparations were examined for protein composition by SDS-PAGE in the presence of β-mercaptoethanol and were found to be free from any detectable contamination by other proteins (data not shown). Membrane fusion actvity of these virosomal preparations was checked by their ability to lyse mouse RBCs in the presence of WGA. F-virosome associated pCIS3CAT DNA was DNAaseI resistant indicating thereby that it was entrapped rather than intercalated or adsorbed within the virosomal membrane. Moreover, the encapsulated DNA was found to be intact and of form I (covalent closed circle form) as shown in FIG. 2. No detectable leakage of DNA was observed from untreated, plasma/FCS treated and heat-treated loaded F-virosomes. Heat-treated F-virosomes were fusion inactive.

Uptake of pCIS3CAT DNA by HepG2 cells through membrane fusion: Southern analysis and quantitation of delivered DNA in various subcellular fractions: F-virosome mediated internalization of pCIS3CAT DNA by cells was examined prior to checking CAT gene expression. After 2 h of fusion and 24 h of growth of HepG2 cells, the amount of DNA delivered by F-virosomes (containing 1 μg and 10 μg of DNA, FIG. 3a) was found to be maximum in nuclear fraction. The amount of DNA delivered to nucleus by heat-treated F-virosomes was 2.6–2.8 times less than that delivered by untreated F-virosomes containing 1 μg and 10 μg DNA respectively. This observation was further confirmed by Southern hybridization of DNA delivered to various subcellular fractions using $^{32}$P-labeled CAT gene probe. The hybridization signal detected from nuclear fraction of HepG2 cells incubated with loaded F-virosomes (FIG. 3b, lane 1) was more than that of the corresponding heat controls (FIG. 3b, lane 4). Also, a very faint signal corresponding to covalent closed circle(ccc) form of DNA was observed in case of heat-treated F-virosome mediated delivery. Heat-treated F-virosomes are known to be fusion-inactive but can behave as liganded proteoliposomes. Heat-treated loaded F-virosomes are non-fusogenic. Therefore they are likely to be taken up by endocytosis leading to their accumulation in lysosomes and subsequent degradation of pCIS3CAT DNA as shown by the insignificant amount of DNA detected in lysosomal/mitochondrial fraction (FIG. 3a and FIG. 3b, lanes 3 and 6). No DNA was detected in cytosolic fraction of HepG2 cells treated with F-virosomes and the corresponding heat control (FIG. 3b, lanes 2 and 5), thereby indicating that most of the DNA delivered by this method is efficiently transferred to nucleus of the cells. No hybridization signal was detected in any subcellular fraction when free DNA was delivered to HepG2 cells (FIG. 3b, lanes 7,8,9) or from subcellular fractions of cells alone (FIG. 3b, lanes 10, 11, 12). These results strongly support the fusion mediated delivery of pCIS3CAT DNA by F-virosomes and efficient transport of the delivered DNA to the nuclear compartment of HepG2 cells.

Expression of CAT gene in HepG2 cells after fusion mediated DNA delivery: structure-function analysis: As shown in FIG. 4a, the amount of CAT protein expressed was found to increase with increasing DNA dose. Also the amount of CAT protein expressed after F-virosome mediated delivery was three times more than the corresponding heat controls in all doses of DNA. The binding of F-virosomes to liver cells is known to be strongly inhibited in the presence of asialiofetuin and hence no CAT protein was detected in HepG2 cells after this treatment. In case of free DNA incubated with HepG2 cells and cells alone, no ELISA signal was detected. One microgram of pCIS3CAT DNA delivered by lipofectin transfection did not express detectable amounts of CAT protein. However, 15 μg of DNA delivered by lipofectin transfection expressed 300 μg of CAT protein which was equal to the amount of protein expressed when 1 μg of DNA was delivered by F-virosomes (FIG. 4b).

CAT assay was performed to check the acetylating activity of CAT protein expressed in HepG2 cells. Varying amounts of cell extracts prepared 24 h after fusion mediated delivery of pCIS3CAT DNA into HepG2 cells were used for CAT assay. CAT activity was determined by the formation of 1-acetyl BODIPY-chloramphenicol derivative (FIG. 5, lanes 1,2,3). In 100 μg of cell extract (Lane 1) signal was faintly visible. In case of controls, for example free DNA incubated with HepG2 cells and cells alone, no CAT activity was detected (Lanes 4 and 5 respectively). In positive controls (500 μg of standard CAT), two monoacetylated derivatives of BODIPY-chloramphenicol were seen (Lane 8). Heat-treated F-virosomes and asialofetuin incubated with HepG2 cells were also included as controls and no detectable activity was detected.

EXAMPLES

Bacterial strains and plasmids: E. coli strain DH5 was used for all transformation experiments. DH5 was grown in Luria-Bertini (LB) broth or LB agar at 37° C. Virus: Sendai (Z strain) was grown in allantoic sac of 10 to 11 day old embryonated chicken eggs. he virus was harvested and purified as described by Peretz et al in (1974) J, Cell Bio 1. 63, 1–11. Purified virus was resuspended in PBS (150 mM) Nacl, 10 mM phosphate, pH 7.4). Viral yield was estimated in terms of protein amount and its activity was checked by aggluntination and lysis of mouse red blood cells. Aliquots of the virus were stored at 70° C.

Figure 1:
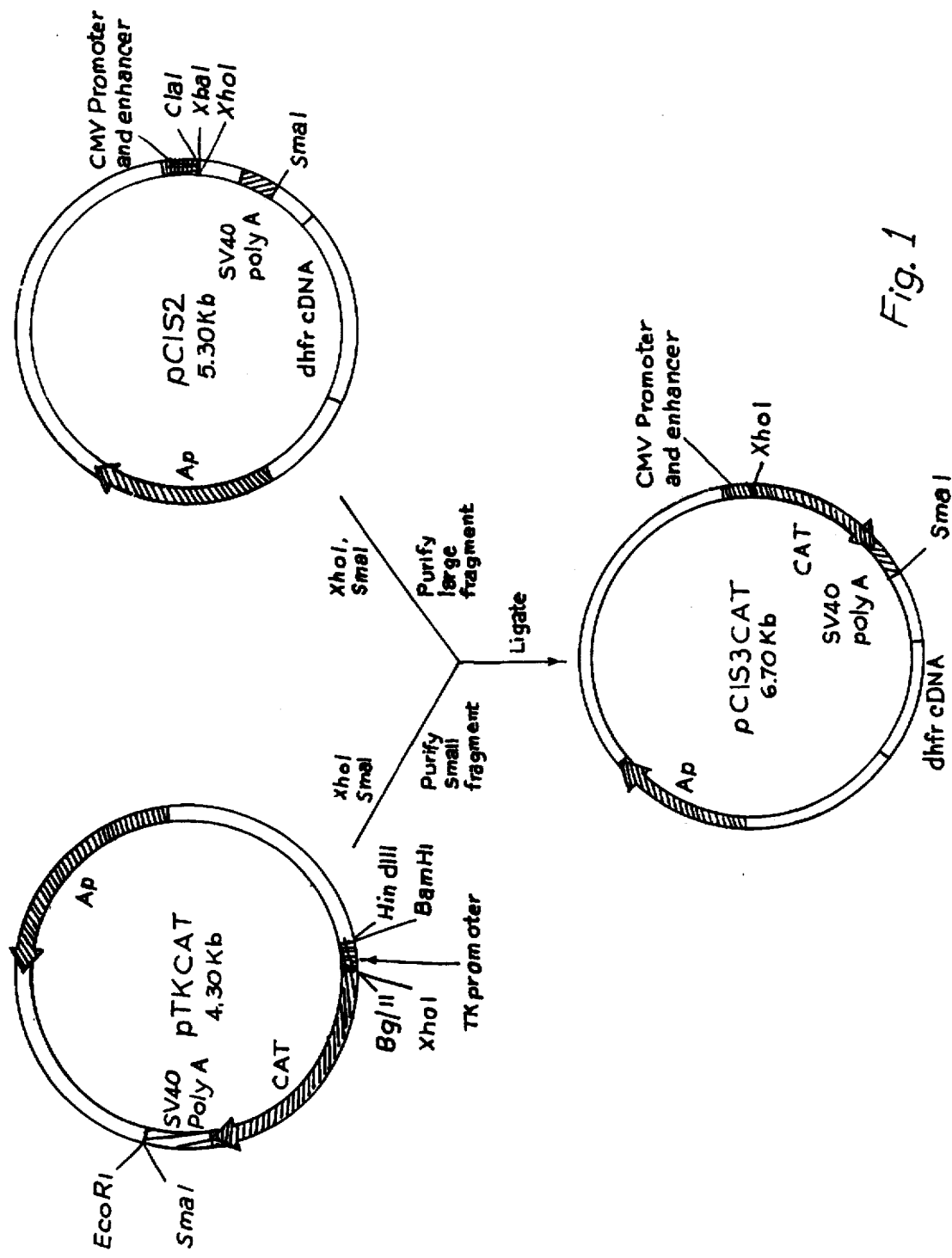
FIG. 1 of the drawings refers to construction of plasmid pCIS3CAT. Relevant restriction sites are shown. Ap, ampicillin; TK, thymidine kinase; dhfr, dihydrofolate reductase; CAT, chloroamphenicol acetyl transferase, CMV, cytomegalovirus.

Cells: HepG2 cells (human hepatoblastoma cell line) were obtained from American Type culture collection and were grown. Fresh red blood cells (RBCs) were obtained from healthy Swiss albino mice. Constructions and isoluation of eukaryotic expression vector: A 1.55-kb XhoI-SmaI fragment from plasmid pTKCAT containing CAT gene and SV40 polyadenylation signal was cloned into the plasmid pCIS2, downstream of the cytomegalovirus promoter-enhancer element. (FIG. 1). Ligation mixture was used to transform E. coli DH5 following a standard protocol. A putative clone was identified and confirmed by restriction mapping and Southern hybridization using P-labeled CAT-gene fragment as a probe. This putative clone was designated as pCIS3CAT. The plasmid pCIS3CAT was isolated and purified by standard alkaline lysis method. DNA concentration was determined by measuring the adsorbance at 260 nm.

We claim:

1. A process for the delivery of a nucleic acid into cells expressing the asialoglycoprotein receptor (ASPG-R) comprising:
   (a) growing Sendai virus;
   (b) harvesting and purifying the Sendai virus;
   (c) preparing reconstituted Sendai viral envelopes comprising F-protein and nucleic acid which are free from contamination by other proteins; and
   (d) incubating the Sendai virus envelopes with cells expressing the asialoglycoprotein receptor (ASPG-R).

2. The process of claim 1 wherein the reconstituted Sendai vital envelopes are produced by a process comprising:
   (a) adding a reducing agent to Sendai virus to reduce the HN protein and to produce a reduced virus;
   (b) subjecting the reduced virus to the step of dialysis to remove the reducing agent;
   (c) solubilizing the reduced virus with a solubilizing agent to obtain a solution;
   (d) centrifuging the solution to separate insolubles consisting of reduced HN protein and the core of said virus;
   (e) adding said nucleic acid to the supernatant; and
   (f) slowly removing the solubilizing agent which leads to the formation of said reconstituted Sendai viral envelope.

3. The process of claim 2 wherein the reducing agent is dithiothreitol (DTT).

4. The process of claim 2 wherein the solubilizing agent is a detergent.

5. The process of claim 2 wherein the dialysis is done in the presence of DTT.

6. The process of claim 2 wherein the solubilizing agent is removed over a six hour period.

7. The process of claim 2 wherein the nucleic acid in the reconstituted Sendai vital envelopes is resistant to degradation by DNAase I.

8. The process of claim 2 wherein said nucleic acid is added to the supernatant at a ratio of 75 micrograms of said nucleic acid per milligram of virus.

9. The process of claim 2 wherein the solubilizing agent is removed with a nonpolar polystyrene adsorbent.

10. The process of claim 9 wherein the ratio of solubilizing agent to adsorbent is 1:8.

11. A process for producing a reconstituted Sendai viral envelope comprising the F-protein, a heterologous nucleic acid and being free from contamination by other proteins, said process comprising:
   (a) adding a reducing agent to Sendai virus to reduce the HN protein and to produce a reduced virus;
   (b) subjecting the reduced virus to the step of dialysis to remove the reducing agent;
   (c) solubilizing the reduced virus with a solubilizing agent to obtain a solution;
   (d) centrifuging the solution to separate insolubles consisting of reduced HN protein and the core of said virus;
   (e) adding said nucleic acid to the supernatant; and
   (f) slowly removing the solubilizing agent which leads to the formation of said reconstituted Sendai viral envelope.

12. The process of claim 11 wherein the reducing agent is dithiothreitol (DTT).

13. The process of claim 11 wherein the solubilizing agent is a detergent.

14. The process of claim 11 wherein the dialysis is done in the presence of DTT.

15. The process of claim 11 wherein the solubilizing agent is removed over a six hour period.

16. The process of claim 11 wherein said nucleic acid is added to the supernatant at a ratio of 75 micrograms of said nucleic acid per milligram of virus.

17. A reconstituted Sendai vital envelope produced by the process of claim 11.

18. The process of claim 11 wherein the solubilizing agent is removed with a nonpolar polystyrene adsorbent.

19. The process of claim 18 wherein the ratio of solubilizing agent to adsorbent is 1:8.

20. A process for producing a reconstituted Sendai viral envelope comprising the F-protein, a heterologous nucleic acid and being free from contamination by other proteins, said process comprising:
   (a) adding DTT to Sendai virus to reduce the HN protein and to produce a reduced virus;
   (b) subjecting the reduced virus to the step of dialysis to remove the DTT;
   (c) solubilizing the reduced virus with a solubilizing agent to obtain a solution;
   (d) centrifuging the solution to separate insolubles consisting of reduced HN protein and the core of said virus;
   (e) adding 75 micrograms of said nucleic acid per milligram of virus to the supernatant; and
   (f) slowly removing the solubilizing agent with a nonpolar polystyrene adsorbent, wherein the ratio of solubilizing agent to adsorbent is 1:8 which leads to the formation of said reconstituted Sendai viral envelope.

21. A reconstituted Sendai vital envelope produced by the process of claim 20.

22. Reconstituted Sendai-viral envelopes comprising the F-protein, a heterologous nucleic acid and being free from contamination by other proteins.

* * * * *